(12) United States Patent
Jiang

(10) Patent No.: US 10,994,069 B1
(45) Date of Patent: May 4, 2021

(54) NOZZLE AND EAR CLEANING DEVICE

(71) Applicant: Shenzhen Zhuzhu Digital Co., Ltd., Shenzhen (CN)

(72) Inventor: Gang Jiang, Chongqing (CN)

(73) Assignee: Shenzhen Zhuzhu Digital Co., Ltd., Shenzhen (CN)

(*) Notice: Subject to any disclaimer, the term of this patent is extended or adjusted under 35 U.S.C. 154(b) by 0 days.

(21) Appl. No.: 17/155,257

(22) Filed: Jan. 22, 2021

(30) Foreign Application Priority Data

Dec. 16, 2020 (CN) .......................... 202023037870.6

(51) Int. Cl.
| | | |
|---|---|---|
| *A61M 3/02* | (2006.01) | |
| *A61M 5/00* | (2006.01) | |
| *A61M 25/00* | (2006.01) | |
| *A61M 31/00* | (2006.01) | |
| *A61M 25/16* | (2006.01) | |
| *A61M 39/02* | (2006.01) | |
| *A61M 27/00* | (2006.01) | |
| *A61K 9/02* | (2006.01) | |

(52) U.S. Cl.
CPC ........ *A61M 3/0279* (2013.01); *A61M 3/0262* (2013.01); *A61M 2210/0662* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,685,851 | A  * | 11/1997 | Murphy ................ | A61M 3/022 604/150 |
| 8,834,408 | B2 * | 9/2014 | Baker ................. | A61M 1/0052 604/27 |
| 8,852,150 | B2 * | 10/2014 | Wang .................. | A61M 3/0279 604/131 |
| 8,936,562 | B2 * | 1/2015 | Kokenis .............. | A61M 3/0279 604/2 |
| 8,986,281 | B2 * | 3/2015 | Koehler ............ | A61M 25/0023 604/508 |
| 9,119,744 | B2 * | 9/2015 | Wellen ................. | A61B 1/2275 |
| 9,578,854 | B2 * | 2/2017 | Kokenis ............... | A01K 13/003 |

FOREIGN PATENT DOCUMENTS

AU      2014211764 B2 *  2/2004

* cited by examiner

*Primary Examiner* — Tatyana Zalukaeva
*Assistant Examiner* — Ilya Y Treyger
(74) *Attorney, Agent, or Firm* — Dority & Manning, P.A.

(57) ABSTRACT

A nozzle and an ear cleaning device are disclosed. The nozzle includes: a main body, where the main body is provided with a first hole portion penetrating in a front-rear direction; and a housing, where the housing is connected to the main body and surrounding a periphery of the main body, the housing is provided with a guide portion and a plurality of drainage portions, the guide portion has an outer diameter gradually increasing from a front end of the main body to a rear end of the main body, the plurality of drainage portions are arranged at intervals in a circumferential direction of the housing, and each of the drainage portions is communicated with the front end of the main body and extends from the front end of the main body toward the rear end of the main body.

20 Claims, 9 Drawing Sheets

NOZZLE AND EAR CLEANING DEVICE

CROSS-REFERENCE TO RELATED APPLICATIONS

This application is based on and claims the benefit of priority from Chinese Patent Application No. 202023037870.6, filed on 16 Dec. 2020, the entirety of which is incorporated by reference herein.

FIELD

The present application relates to the technical field of personal care products, and in particular, to a nozzle and an ear cleaning device.

BACKGROUND

Earwax is generated in human ears. If it is not removed in time, it will cause hearing damage. In the past, people usually used cotton swabs or the like to remove earwax. However, the earwax cannot be completely removed using cotton swabs or the like. In view of this, a cleaning spray gun for removing earwax is produced. The known spray guns for ear cleaning usually include a bottle for containing cleaning liquid, a pump for sucking the liquid, a nozzle for being inserted into the human ear and injecting the liquid, and a conduit that connects the pump to the nozzle.

To enable the liquid injected into the ear to flow out, the nozzle of the known cleaning spray gun is generally elongated. However, if the elongated nozzle is operated incorrectly, the nozzle may touch the eardrum, which may cause ear injury.

SUMMARY

To solve the above technical problems, the present application provides a nozzle, which can be easily inserted into the ear and enables the liquid to flow out easily, and can prevent ear injury.

The nozzle according to an embodiment of a first aspect of the present application includes: a main body provided with a first hole portion penetrating in a front-rear direction; and a housing connected to the main body and surrounding a periphery of the main body, where the housing is provided with a guide portion and a plurality of drainage portions, the guide portion has an outer diameter gradually increasing from a front end of the main body to a rear end of the main body, the plurality of drainage portions are arranged at intervals in a circumferential direction of the housing, and each of the drainage portions is communicated with the front end of the main body and extends from the front end of the main body toward the rear end of the main body.

The nozzle according to the embodiment of the first aspect of the present application has the following beneficial effects: Because the housing is provided with the guide portion and the drainage portions, the nozzle can be easily inserted into the ear and enables the liquid to flow out easily, and can prevent ear injury.

In some embodiments, a front end of the housing and the front end of the main body are integrally formed.

In some embodiments, a cavity is formed between an inner side of a rear end of the housing and the periphery of the rear end of the main body.

In some embodiments, the drainage portion penetrates through the housing and is communicated with the cavity.

In some embodiments, a plurality of ribs are arranged in the cavity, and the ribs are connected to the main body and the housing respectively, arranged at intervals around the periphery of the main body and staggered relative to the drainage portions in the circumferential direction of the main body.

In some embodiments, the first hole portion includes: a circular hole portion arranged at the rear end of the main body; and a tapered hole portion arranged at the front end of the main body, where the tapered hole portion gradually increasing from the front end of the main body to the rear end of the main body, and a rear end of the tapered hole portion and the circular hole portion are in smooth transition.

In some embodiments, the front end of the main body is provided with a blocking portion for blocking a part of an outlet end of the first hole portion.

In some embodiments, the blocking portion is configured to block a middle portion of the outlet end of the first hole portion in an axial direction.

In some embodiments, a gap is formed between the blocking portion and the outlet end of the first hole portion in a front-rear direction.

In some embodiments, the rear end of the main body is provided with a mounting portion extending out in a rearward direction relative to the housing.

An ear cleaning device according to an embodiment of a second aspect of the present application includes: a bottle body, configured to store liquid for cleaning ears; a pump, configured to pump liquid and mounted at a bottle opening of the bottle body;

and any above nozzle connected to a liquid outlet of the pump.

In some embodiments, the ear cleaning device further includes a conduit, where one end of the conduit is detachably mounted at the liquid outlet of the pump, and the nozzle is detachably mounted at the other end of the conduit.

In some embodiments, the ear cleaning device further includes a transfer element, where one end of the transfer element is embedded into the other end of the conduit, and the nozzle is detachably mounted at the other end of the transfer element.

DETAILED DESCRIPTION OF THE EMBODIMENTS

Figure 1:
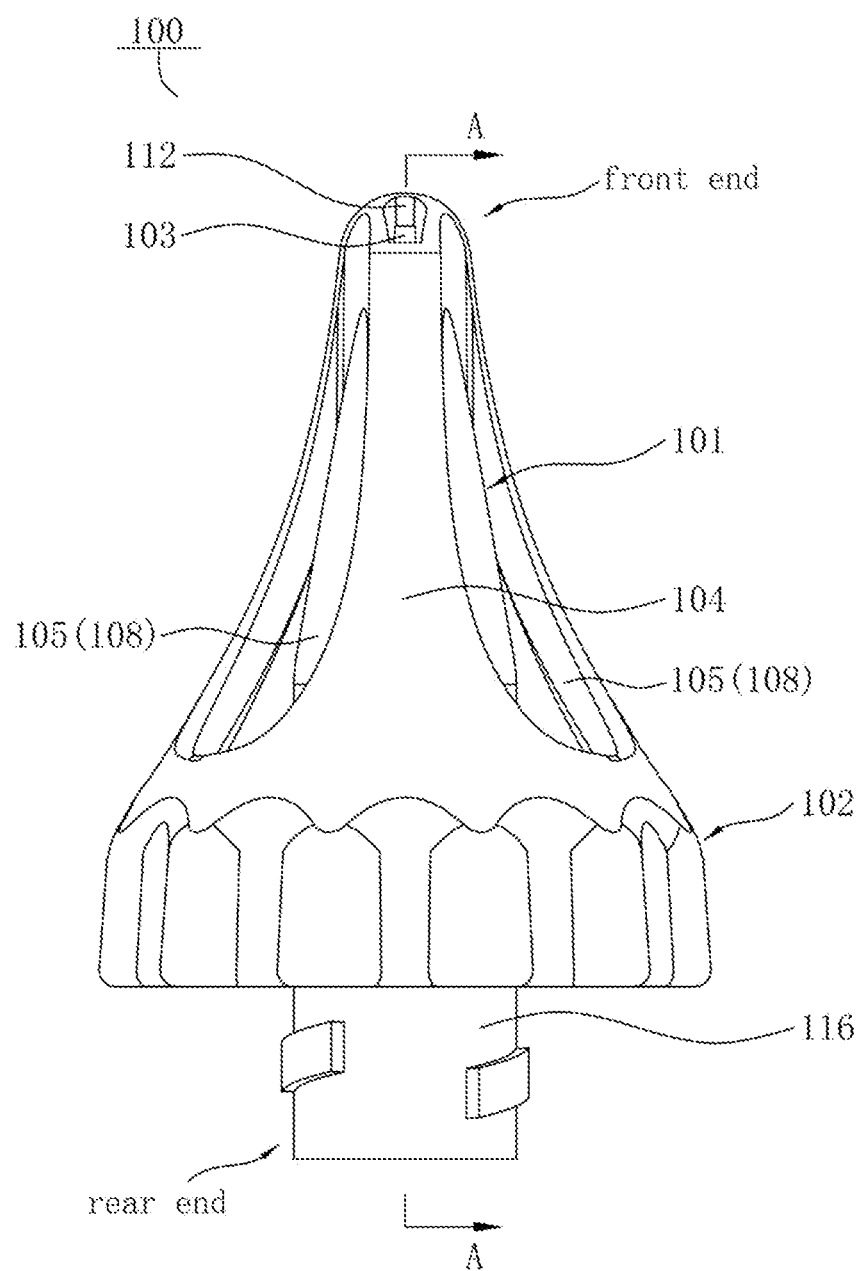
FIG. 1 is a front view of a nozzle according to an embodiment in a first aspect of the present application.

Embodiments of the present application are described in detail below. Examples of the embodiments are shown in the accompanying drawings, in which the same or similar reference numerals refer to the same or similar elements or elements having the same or similar functions. The embodiments described below with reference to the accompanying drawings are examples and are merely intended to explain the present application, and cannot be understood as limiting the present application.

In the description of the present application, it should be understood that if orientation description is involved, the orientation or position relationship indicated by, for example, "up", "down", "front", "rear", "left" and "right" is based on the orientation or position relationship shown in the drawings, and these terms are merely used to facilitate description of the present application and simplify the description, but not to indicate or imply that the mentioned device or elements must have a specific orientation and must be established and operated in a specific orientation, and thus, these terms cannot be understood as a limitation to the present application.

In the description of the present application, "several" means one or more, and "a plurality of" means at least two. "More than", "less than", "exceeding, and the like" are understood as excluding this number, and "above", "below", "within", and the like are understood as including this number. "First" and "second" in description are only for the purpose of distinguishing between technical features, and cannot be understood as indicating or implying relative importance or implicitly indicating the number of technical features indicated or implicitly indicating the sequence relationship of indicated technical features.

In the description of the present application, unless otherwise explicitly defined, the words such as "setting", "mounting" and "connection" should be understood in a broad sense, and those skilled in art can properly determine the specific meanings of the above words in the present application with reference to the specific contents of the technical solution.

Figure 2:
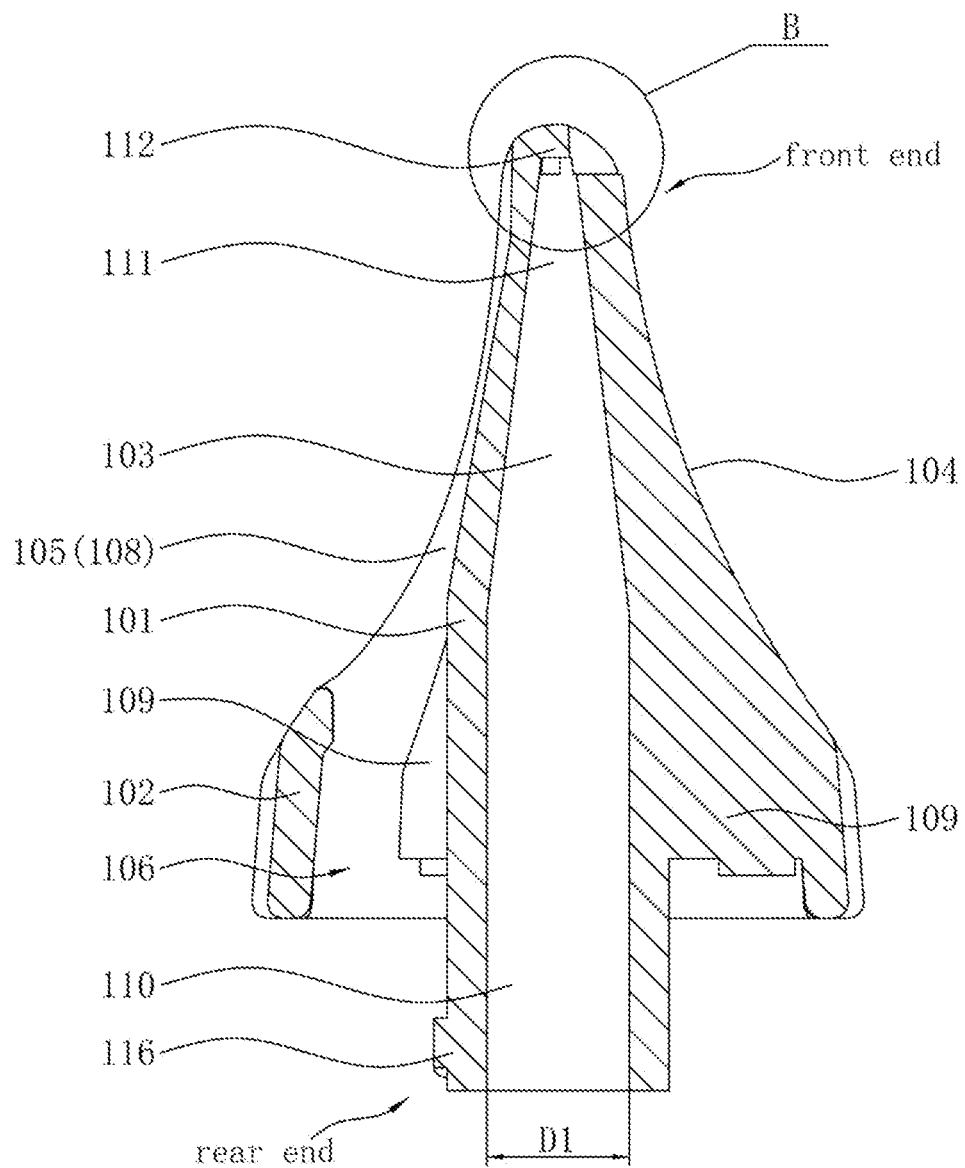
FIG. 2 is a cross-sectional view along line A-A in FIG. 1.
Figure 3:
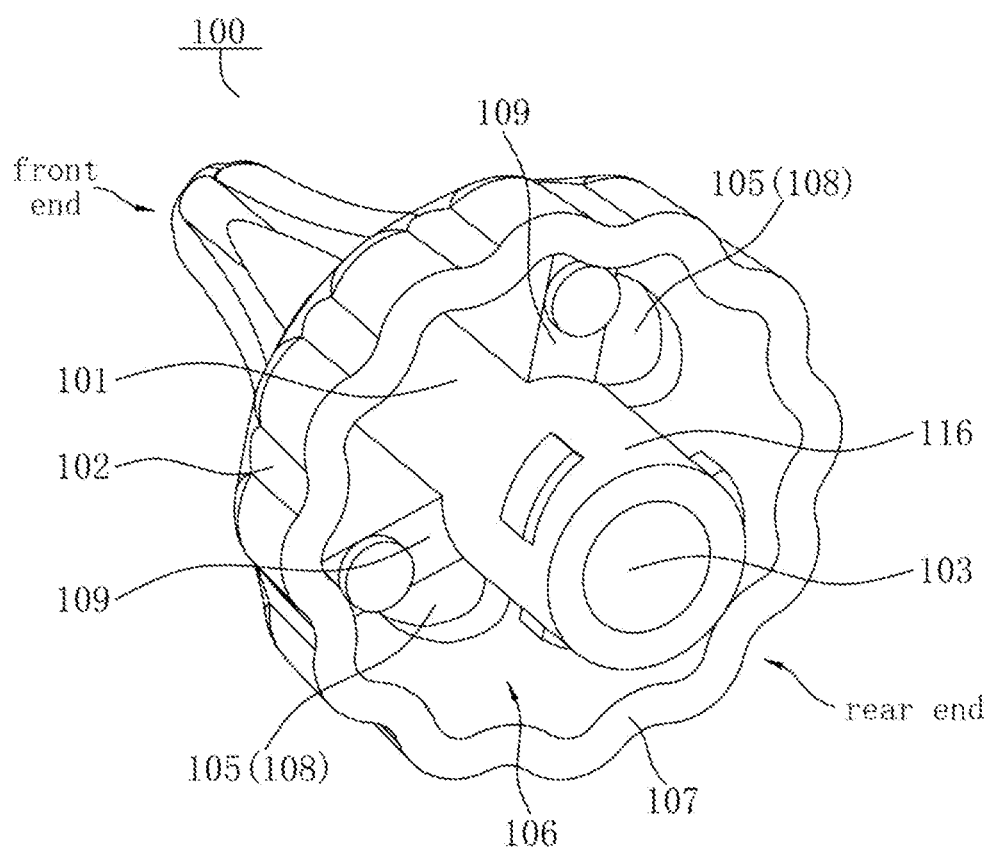
FIG. 3 is a perspective view of the nozzle in FIG. 1.

FIG. 1 is a front view of a nozzle 100; FIG. 2 is a cross-sectional view along line A-A in FIG. 1; and FIG. 3 is a perspective view of the nozzle 100. Referring to FIG. 1 to FIG. 3, the nozzle 100 according to an embodiment in a first aspect of the present application includes: a main body 101 and a nozzle 102, where the main body 101 is provided with a first hole portion 103 penetrating in a front-rear direction; the housing 102 is connected to the main body 101 and surrounds a periphery of the main body 101, the housing 102 is provided with a guide portion 104 and a plurality of drainage portions 105, the guide portion 104 has an outer diameter gradually increasing from a front end of the main body 101 to a rear end of the main body 101, the plurality of drainage portions 105 are arranged at intervals in a circumferential direction of the housing 102, and each of the drainage portions 105 is communicated with the front end of the main body 101 and extends from the front end of the main body 101 toward the rear end of the main body 101.

In this embodiment, because the housing 102 is provided with the guide portion 104 and the drainage portions 105, the nozzle can be easily inserted into the ear and enables the liquid to flow out easily, and can prevent ear injury. Specifically, the outer diameter of the guide portion 104 gradually increases from the front end of the main body 101 toward the rear end of the main body 101, so that the depth that the nozzle 100 can reach into the ear is limited while the nozzle 100 can be easily inserted into the ear, thereby preventing ear injury. In addition, the guide portion 104 can prevent the liquid ejected through the first hole portion 103 from splashing to a certain extent. The housing 102 is provided with the plurality of drainage portions 105, which can easily make the liquid flow back.

For ease of description, one end of the nozzle 100 inserted into the ear is taken as a front end, and one end of the nozzle 100 connected to a pump 202 described later is taken as a rear end.

In some embodiments, to easily form the main body 101 and the housing 102, a front end of the housing 102 and the front end of the main body 101 are integrally formed. Specifically, the housing 102 and the main body 101 may be integrally formed through, for example, injection molding. The materials of the housing 102 and the main body 101 are not particularly limited provided that they are suitable for use by the human body and have elasticity. For example, they may be thermoplastic elastic materials such as TPE, TPR, TPU, and TPEE. The rear end of the main body 101 is cylindrical, the front end of the main body 101 is conical, and the front end and the rear end of the main body 101 are in smooth transition. The housing 102 extends from the conical front end of the main body 101 toward the rear end of the main body 101. The front end of the main body 101 is set into the conical shape, so that the thickness of the front end of the housing 102 increases when the front end of the housing 102 and the front end of the main body 101 are integrally formed. The housing 102 is shaped like a nipple as a whole, a peripheral portion of the front end of the housing 102 is arc-shaped, and the arc-shaped peripheral portion of the housing 102 is used as the guide portion 104, so that the outer diameter of the guide portion 104 gradually increases from the front end of the main body 101 toward the rear end of the main body 101.

In some embodiments, a cavity 106 is formed between an inner side of a rear end of the housing 102 and the periphery of the rear end of the main body 101, so that the housing 102 can be easily deformed. Specifically, the rear end of the housing 102 is provided with an annular thin wall 107, and the cavity 106 is formed between the annular thin wall 107 and the cylindrical rear end of the main body 101. As such, when the rear end of the housing 102 is compressed, the rear end of the housing 102 can be easily compressed toward the main body 101, thereby ensuring that the housing 102 can be effectively compressed and preventing the housing 102 from causing discomfort to the ear. Further, the thin wall 107 may form a plurality of wrinkles distributed in the circumferential direction of the housing 102, so that the rear end of the housing 102 is more easily compressed toward the main body 101.

In some embodiments, to enable the drainage portion 105 to easily drain the liquid out, the drainage portion 105 penetrates through the housing 102 and is communicated with the cavity 106. Specifically, the drainage portion 105 may include a through groove 108 that penetrates through at least a part of the housing 102 in the front-rear direction. The through groove 108 penetrates through the housing 102 along the front end so that a front end of the through groove 108 is close to the front end of the first hole portion 103. When the front end of the nozzle 100 extends into the ear, the front end of the through groove 108 is close to a position where the nozzle 100 injects the liquid (namely, a position of the front end of the first hole portion 103). As such, the liquid flowing out from the ear can be easily received. In addition, because the rear end of the housing 102 is used to block the ear, the drainage portion 105 penetrates through the housing 102 along the rear end of the housing 102 and is connected to the cavity 106, so that it can be ensured that the liquid can effectively flow out.

The number of the through grooves 108 as the drainage portions 105 is not particularly limited provided that they enable the liquid to flow out easily and are easy to operate.

For example, there may be three through grooves, which are evenly arranged at intervals in the circumferential direction of the housing 102. In addition, although the through groove 108 is used as the drainage portion 105 as an example, the description is not limited to this. The drainage portion 105 may be directly provided with a plurality of grooves (not shown) in the periphery of the housing 102 as drainage grooves.

Still referring to FIG. 3, in some embodiments, to enhance the strength of the housing 102 to a certain extent, a plurality of ribs 109 are arranged in the cavity 106, and the ribs 109 are connected to the main body 101 and the housing 102 respectively. Specifically, the ribs 109 may also be integrally formed with the main body 101 and the housing 102 respectively. The shape of the rib 109 is set according to the shape of the cavity 106. For example, when the housing 102 is in the shape of a nipple as a whole, the cross section of the cavity 106 also gradually increases from the front end to the rear end. Therefore, the cross section of the rib 109 also gradually increases from the front end of the inner side of the housing 102 to the rear end of the inner side of the housing 102.

In some embodiments, to prevent the ribs 109 from blocking the liquid, the ribs 109 are arranged at intervals around the periphery of the main body 101 and staggered relative to the drainage portions 105 in the circumferential direction of the main body 101. Specifically, for example, corresponding to the three through grooves 108, there may be also three ribs 109, and the ribs 109 and the through grooves 108 are staggered along the periphery of the main body 101.

Still referring to FIG. 2, in some embodiments, to increase the impact of the liquid, the first hole portion 103 includes: a circular hole portion 110 and a tapered hole portion 111, where the circular hole portion 110 is arranged at the rear end of the main body 101; the tapered hole portion 111 is arranged at the front end of the main body 101, the tapered hole portion 111 has an inner diameter gradually increasing from the front end of the main body 101 to the rear end of the main body 101, and a rear end of the tapered hole portion 111 and the circular hole portion 110 are in smooth transition. Specifically, the diameter D1 of the circular hole portion 110 may be set to, for example, 4-5 mm, and the diameter D2 of the front end of the tapered hole portion 111 (namely an outlet end 103a of the first hole portion 103 (referring to FIG. 5)) is, for example, 1-2 mm. The liquid entering the circular hole portion 110 of the first hole portion 103 is ejected after passing through the tapered hole portion 111, so that the impact force of the liquid can be increased.

Figure 4:
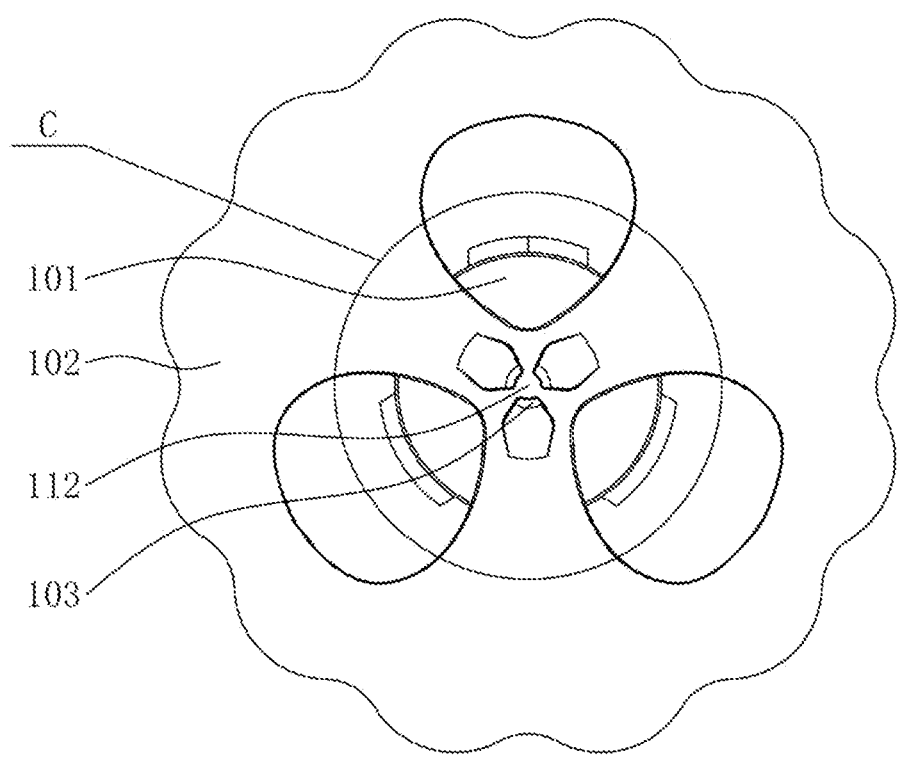
FIG. 4 is a top view of the nozzle in FIG. 1.
Figure 5:
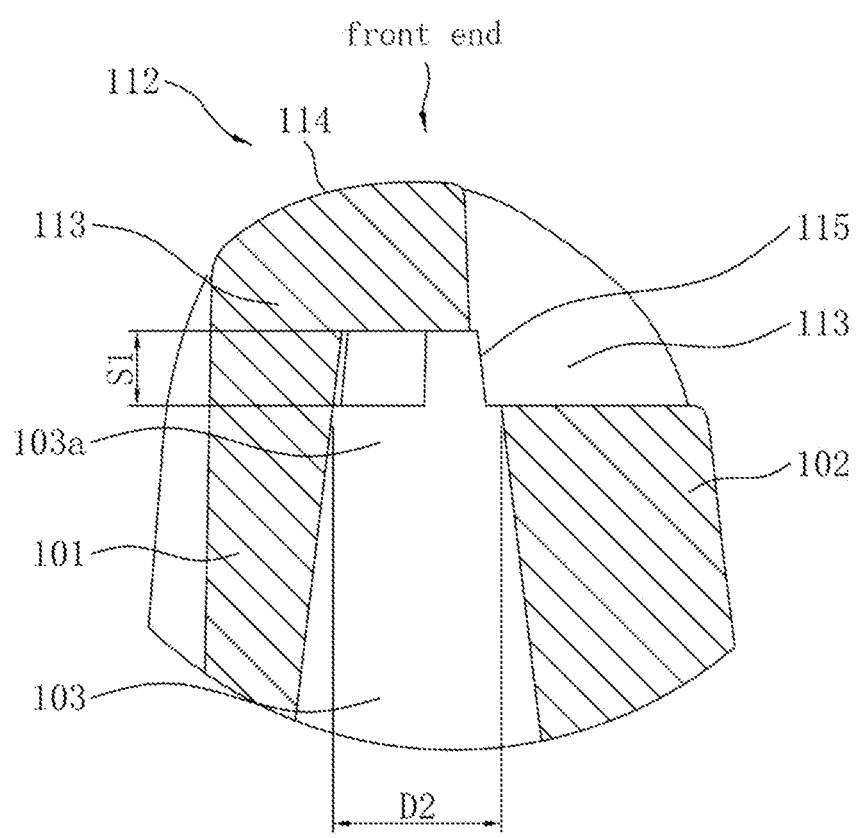
FIG. 5 is a partial enlarged view of a portion B in FIG. 2.
Figure 6:
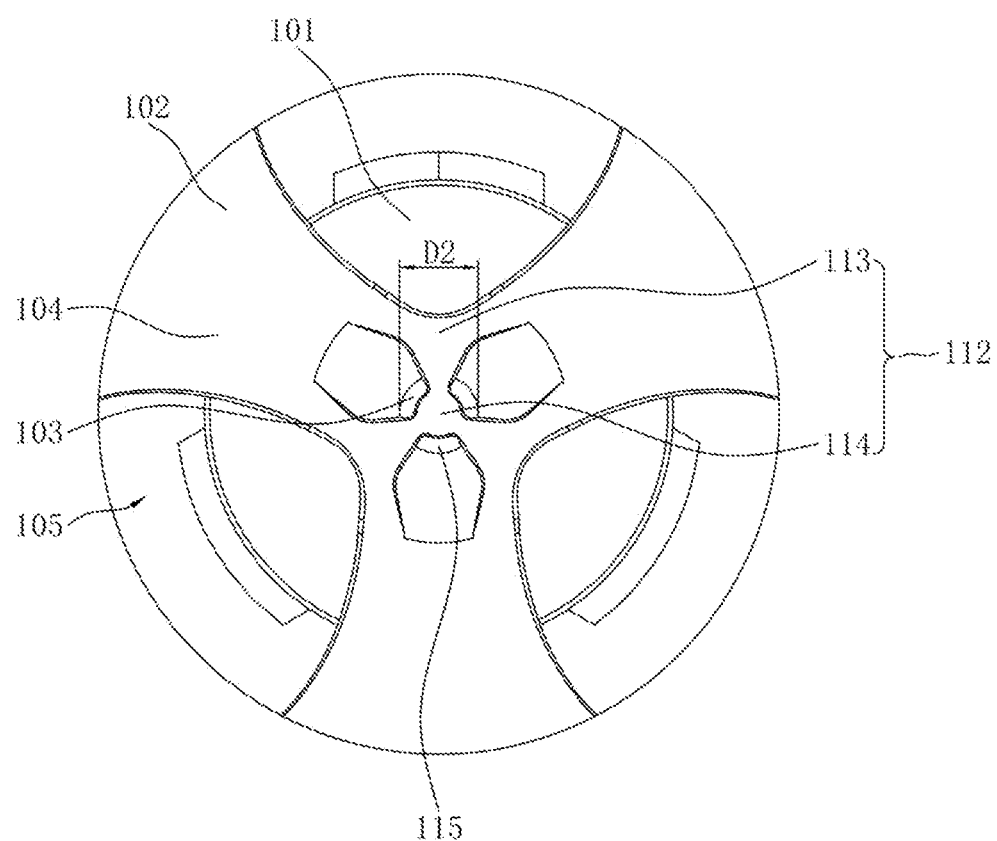
FIG. 6 is a partial enlarged view of a portion C in FIG. 4.
Figure 7:
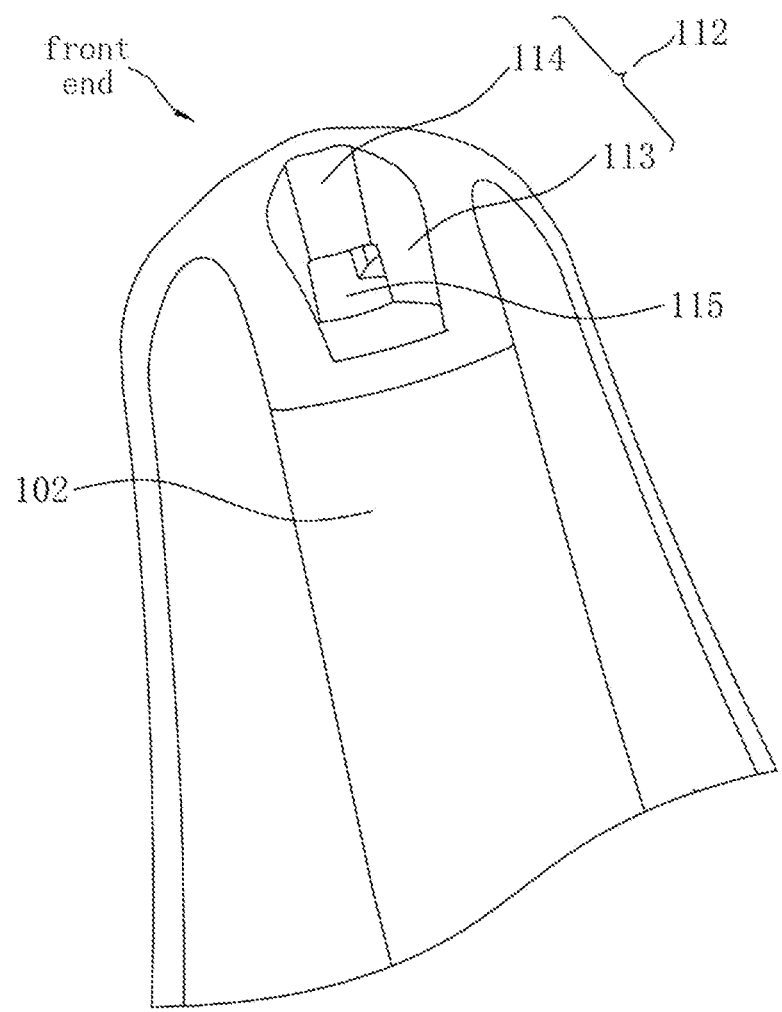
FIG. 7 is an enlarged view of a blocking portion of the nozzle.

FIG. 4 is a top view of the nozzle 100, FIG. 5 is a partial enlarged view of a portion B in FIG. 2, FIG. 6 is a partial enlarged view of a portion C in FIG. 4, and FIG. 7 is an enlarged view of a blocking portion 112 of the nozzle 100. Referring to FIG. 4 to FIG. 7, in some embodiments, to limit the flow rate of the liquid ejected, the front end of the main body 101 is provided with the blocking portion 112, and the blocking portion 112 blocks a part of the outlet end 103a of the first hole portion 103. Specifically, the front end of the housing 102 may be set as the wrapped front end of the main body 101, and the blocking portion 112 and the housing 102 are integrally formed and arranged at the front end of the main body 101. The blocking portion 112 includes a plurality of supporting walls 113 and a blocking member 114 respectively connected to the supporting walls 113, where the plurality of supporting walls 113 are respectively integrally formed at the front end of the housing 102, and arranged at intervals in the circumferential direction of the housing 102, and the blocking member 114 is located in front of the outlet end 103a of the first hole portion 103, and integrally formed with each of the supporting walls 113. As such, the blocking member 114 of the blocking portion 112 blocks a part of the outlet end 103a of the first hole portion 103. Therefore, when the liquid is ejected straight in the axial direction of the first hole portion 103, at least a part of the liquid can be blocked by the blocking member 114 of the blocking portion 112, thereby the flow rate of the liquid ejected can be controlled.

Still referring to FIG. 6, further, the blocking member 114 may be arranged to block a middle portion of the outlet end 103a of the first hole portion 103 in an axial direction. Specifically, for example, there are three supporting walls 113, which are evenly distributed in the circumferential direction of the housing 102. The blocking member 114 is set to be slightly smaller than the outlet end 103a of the first hole portion 103. As such, when the outlet end 103a of the first hole portion 103 is viewed from the front end to the rear end, three slits 115 are formed between the first hole portion 103 and the blocking member 114. Three water flows can be sprayed out through the three slits 115, and the three water flows can mainly clean the periphery inside the ear canal rather than the middle portion of the ear canal. Therefore, the water flows can be prevented from violently impacting on the eardrum and causing ear damage, and surrounding earwax in the ear canal can be effectively removed.

Still referring to FIG. 5, further, to prevent the outlet end 103a of the first hole portion 103 from being blocked, a gap is formed between the blocking portion 112 and the outlet end 103a of the first hole portion 103 in the front-rear direction. Specifically, a distance 51 between the outlet end 103a of the first hole portion 103 and the blocking member 114 of the blocking portion 112 in the front-rear direction is set to, for example, 0.5-1 mm. As such, the slit 115 is inclined with respect to the axial direction of the first hole portion 103, and the area of the slit 115 is enlarged to a certain extent, thereby preventing the outlet end 103a of the first hole portion 103 from being blocked. In addition, since the ejection angle of the water flow is changed, the water flow is at a certain angle with respect to the axial direction of the first hole portion 103. Therefore, the water flows can be further prevented from violently impacting on the eardrum and causing ear damage, and the surrounding earwax in the ear canal can be further effectively removed.

Still referring to FIG. 1 to FIG. 3, in some embodiments, to easily mount the nozzle 100, the rear end of the main body 101 is provided with a mounting portion 116, and the mounting portion 116 extends out in a rearward direction relative to the housing 102. Specifically, the cylindrical rear end of the main body 101 may be provided with a portion extending out rearward with respect to the housing 102 as the mounting portion 116. The mounting portion 116 may be provided with various known connection structures such as a Luer joint structure, a pipe joint structure, and a buckle structure.

Figure 8:
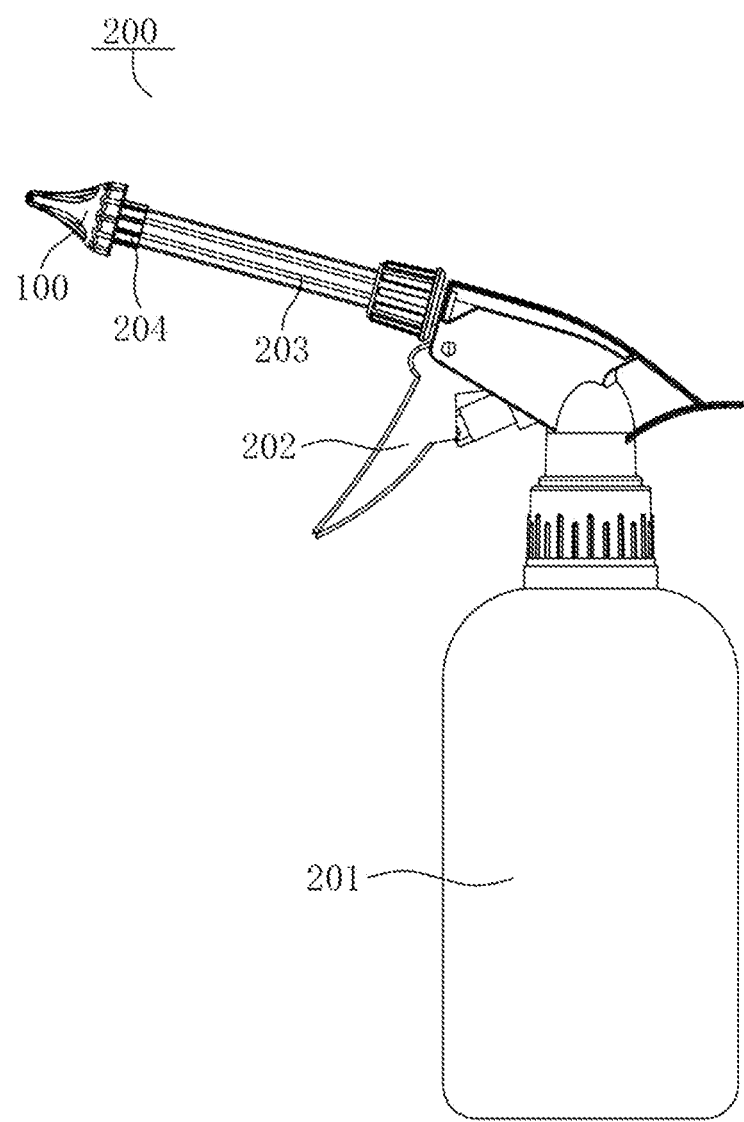
FIG. 8 is a schematic diagram of an ear cleaning device according to an embodiment in a second aspect of the present application.
Figure 9:
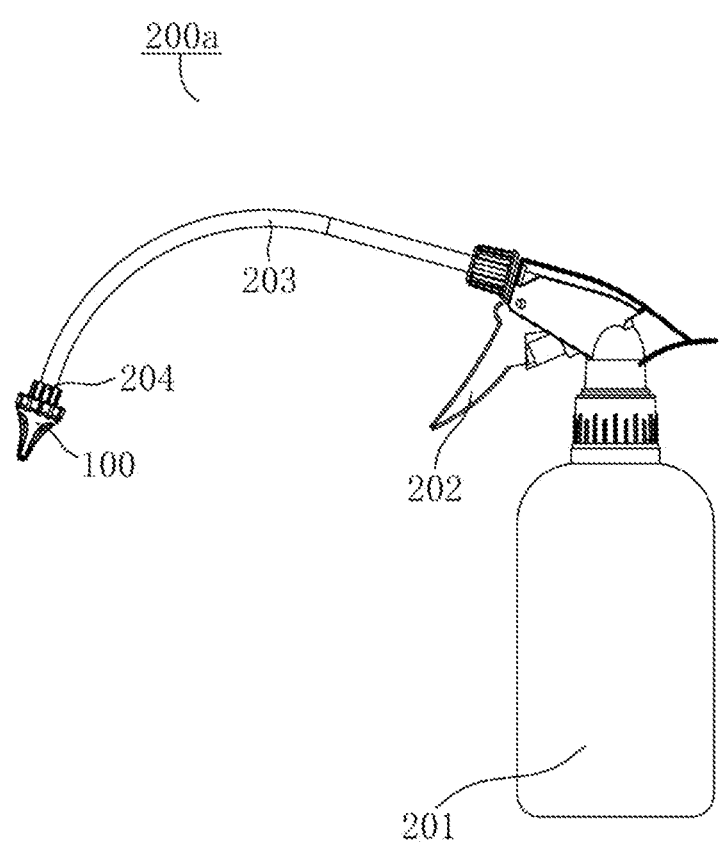
FIG. 9 is a schematic diagram of the ear cleaning device according to another embodiment in the second aspect of the present application.

FIG. 8 is a schematic diagram of an ear cleaning device 200. FIG. 9 is a schematic diagram of an ear cleaning device 200a. Referring to FIG. 8 and FIG. 9, the nozzle 100 according to each of the above embodiments can be used in the ear cleaning device 200. Specifically, an ear cleaning device 200 according to an embodiment in a second aspect of the present application includes: a bottle body 201, a pump 202, and a nozzle 100, where the bottle body 201 is configured to store liquid for cleaning the ears; the pump 202 is configured to pump liquid and mounted at a bottle opening of the bottle body 201; and the nozzle 100 is connected to a liquid outlet of the pump 202.

Specifically, the ear cleaning device 200 may be, for example, a spray gun for ear cleaning.

Specifically, the nozzle 100 can be directly and detachably mounted at the liquid outlet of the pump 202. For example, the liquid outlet end of the pump 202 may be provided with a Luer joint structure, a pipe joint structure, a buckle structure, or the like corresponding to the mounting portion 116 of the nozzle 100, so that the nozzle 100 can be directly mounted to the liquid outlet of the pump 202 or is detachable relative to the liquid outlet of the pump 202.

In addition, the type of the pump 202 for sucking the liquid is not particularly limited. For example, a commercially available pump for sucking the liquid in the bottle can be used.

In addition, in some embodiments, to easily operate the ear cleaning device 200 and prevent the spray gun from colliding with the human head, or the like, the ear cleaning device may further include a conduit 203, where one end of the conduit 203 is detachably mounted at the liquid outlet of the pump 202, and the nozzle 100 is detachably mounted at the other end of the conduit 203. The conduit 203 may use a tube having certain rigidity (referring to FIG. 8) or a flexible tube (referring to FIG. 9). The materials of the conduit 203 are not particularly limited provided that they are suitable for the human body. For example, they may be thermoplastic elastic materials such as TPE, TPR, TPU, and TPEE. In addition, the material of the conduit 203 may also be a metal material, such as a stainless steel material.

In some embodiments, to easily mount the nozzle 100, the ear cleaning device further includes a transfer element 204, where one end of the transfer element 204 is embedded into the other end of the conduit 203, and the nozzle 100 is detachably mounted at the other end of the transfer element 204. Specifically, the transfer element 204 may be made of a relatively hard plastic material such as a PC material. One end of the transfer element 204 is provided with a shaft portion (not shown) that can be embedded into the other end of the conduit 203, and the other end of the transfer element 204 is provided with, for example, a Luer joint structure, a pipe joint structure, or a buckle structure for mounting the nozzle 100. The shaft portion of the transfer element 204 can be connected to the conduit 203 by interference fit. In the case of interference fit between the shaft portion of the transfer element 204 and the conduit 203, the transfer element 204 can be rotated with respect to the conduit 203 in a vigorous manner, so as to prevent the situation that when the nozzle 100 is mounted on the transfer element 204, damage is caused to, for example, a joint due to excessive force. Certainly, to prevent misoperation by an operator, the shaft portion of the transfer member 204 and the conduit 203 may also be fixed by, for example, glue bonding.

In the description of this specification, descriptions with reference to the terms "one embodiment", "some embodiments", "schematic embodiment", "example", "specific example", or "some examples" mean that specific features, structures, materials or characteristics described with reference to this embodiment or example are included in at least one embodiment or example of the present application. In this specification, the illustrative expressions of the above terms do not necessarily refer to the same embodiments or examples. Furthermore, the specific features, structures, materials or characteristics described may be combined in any one or more embodiments or examples in a suitable manner.

Although embodiments of the present application have been shown and described, it can be understood by those of ordinary skill in the art that various changes, modifications, replacements and variations can be made to these embodiments without departing from the principles and purpose of the present application. The scope of the present application is defined by the claims and equivalents thereof.

What is claimed is:

1. A nozzle, comprising:
   a main body, wherein the main body is provided with a first hole portion penetrating in a front-rear direction; and
   a housing, wherein the housing is connected to the main body and surrounding a periphery of the main body, the housing is provided with a guide portion and a plurality of drainage portions, the guide portion has an outer diameter gradually increasing from a front end of the main body to a rear end of the main body, the plurality of drainage portions are arranged at intervals in a circumferential direction of the housing, and each of the drainage portions is communicated with the front end of the main body and extends from the front end of the main body toward the rear end of the main body.

2. The nozzle of claim 1, wherein a front end of the housing and the front end of the main body are integrally formed.

3. The nozzle of claim 2, wherein a cavity is formed between an inner side of a rear end of the housing and the periphery of the main body at the rear end of the main body.

4. The nozzle of claim 3, wherein the drainage portion penetrates through the housing and is communicated with the cavity.

5. The nozzle of claim 3, wherein a plurality of ribs are arranged in the cavity, and the ribs are connected to the main body and the housing respectively, arranged at intervals around the periphery of the main body and staggered relative to the drainage portions in the circumferential direction of the main body.

6. The nozzle of claim 1, wherein the first hole portion comprises:
   a circular hole portion arranged at the rear end of the main body; and
   a tapered hole portion arranged at the front end of the main body, wherein the tapered hole portion has an inner diameter gradually increasing from the front end of the main body to the rear end of the main body, and a rear end of the tapered hole portion and the circular hole portion are in smooth transition.

7. The nozzle of claim 1, wherein the front end of the main body is provided with a blocking portion for blocking a part of an outlet end of the first hole portion.

8. The nozzle of claim 7, wherein the blocking portion is configured to block a middle portion of the outlet end of the first hole portion in an axial direction.

9. The nozzle of claim 8, wherein a gap is formed between the blocking portion and the outlet end of the first hole portion in a front-rear direction.

10. The nozzle of claim 1, wherein the rear end of the main body is provided with a mounting portion extending out in a rearward direction relative to the housing.

11. An ear cleaning device, comprising:
    a bottle body, configured to store liquid for cleaning ears;
    a pump, configured to pump liquid and mounted at a bottle opening of the bottle body; and
    a nozzle connected to a liquid outlet of the pump, the nozzle comprising:

a main body, wherein the main body is provided with a first hole portion penetrating in a front-rear direction; and a housing, wherein the housing is connected to the main body and surrounding a periphery of the main body, the housing is provided with a guide portion and a plurality of drainage portions, the guide portion has an outer diameter gradually increasing from a front end of the main body to a rear end of the main body, the plurality of drainage portions are arranged at intervals in a circumferential direction of the housing, and each of the drainage portions is communicated with the front end of the main body and extends from the front end of the main body toward the rear end of the main body.

12. The ear cleaning device of claim 11, wherein a front end of the housing and the front end of the main body are integrally formed.

13. The ear cleaning device of claim 12, wherein a cavity is formed between an inner side of a rear end of the housing and the periphery of the main body at the rear end of the main body, and the drainage portion penetrates through the housing and is communicated with the cavity.

14. The ear cleaning device of claim 13, wherein a plurality of ribs are arranged in the cavity, and the ribs are connected to the main body and the housing respectively, arranged at intervals around the periphery of the main body and staggered relative to the drainage portions in the circumferential direction of the main body.

15. The ear cleaning device of claim 11, wherein the first hole portion comprises:

a circular hole portion arranged at the rear end of the main body; and a tapered hole portion arranged at the front end of the main body, wherein the tapered hole portion has an inner diameter gradually increasing from the front end of the main body to the rear end of the main body, and a rear end of the tapered hole portion and the circular hole portion are in smooth transition.

16. The ear cleaning device of claim 11, wherein the front end of the main body is provided with a blocking portion for blocking a part of an outlet end of the first hole portion, and the blocking portion is configured to block a middle portion of the outlet end of the first hole portion in an axial direction.

17. The ear cleaning device of claim 16, wherein a gap is formed between the blocking portion and the outlet end of the first hole portion in a front-rear direction.

18. The ear cleaning device of claim 11, wherein the rear end of the main body is provided with a mounting portion extending out in a rearward direction relative to the housing.

19. The ear cleaning device of claim 11, further comprising a conduit, wherein one end of the conduit is detachably mounted at the liquid outlet of the pump, and the nozzle is detachably mounted at the other end of the conduit.

20. The ear cleaning device of claim 12, further comprising a transfer element, wherein one end of the transfer element is embedded into the other end of the conduit, and the nozzle is detachably mounted at the other end of the transfer element.

* * * * *